(12) United States Patent
Dray et al.

(10) Patent No.: US 10,980,404 B2
(45) Date of Patent: Apr. 20, 2021

(54) DEVICE AND METHOD FOR PRODUCING A NUMERICAL CLASSIFIER OF IMAGES, SO AS TO DETERMINE THE VIEWING QUALITY OF THE ENDOSCOPIC VIDEOCAPSULE IMAGES OF A SEGMENT OF THE DIGESTIVE TUBE

(71) Applicants: ASSISTANCE PUBLIQUE-HOPITAUX DE PARIS, Paris (FR); SORBONNE UNIVERSITÉ, Paris (FR); ÉCOLE NATIONALE SUPÉRIEURE DE L'ÉLECTRONIQUE ET DE SES APPLICATIONS, Cergy (FR); CENTRE NATIONAL DE LA RECHERCHE SCIENTIFIQUE, Paris (FR); CY CERGY PARIS UNIVERSITÉ, Cergy (FR)

(72) Inventors: Xavier Dray, Paris (FR); Aymeric Histace, Menucourt (FR)

(73) Assignees: ASSISTANCE PUBLIQUE-HOPITAUX DE PARIS, Paris (FR); SORBONNE UNIVERSITÉ, Paris (FR); ÉCOLE NATIONALE SUPÉRIEURE DE L'ÉLECTRONIQUE ET DE SES APPLICATIONS, Cergy (FR); CENTRE NATIONAL DE LA RECHERCHE SCIENTIFIQUE, Paris (FR); CY CERGY PARIS UNIVERSITÉ, Paris (FR)

( * ) Notice: Subject to any disclaimer, the term of this patent is extended or adjusted under 35 U.S.C. 154(b) by 0 days.

(21) Appl. No.: 16/979,252

(22) PCT Filed: Mar. 13, 2019

(86) PCT No.: PCT/EP2019/056295
§ 371 (c)(1),
(2) Date: Sep. 9, 2020

(87) PCT Pub. No.: WO2019/175248
PCT Pub. Date: Sep. 19, 2019

(65) Prior Publication Data
US 2020/0397238 A1 Dec. 24, 2020

(30) Foreign Application Priority Data
Mar. 14, 2018 (EP) .................................. 18305275

(51) Int. Cl.
*A61B 1/04* (2006.01)
*G06N 20/20* (2019.01)
*A61B 1/00* (2006.01)

(52) U.S. Cl.
CPC .......... *A61B 1/041* (2013.01); *A61B 1/00009* (2013.01); *G06N 20/20* (2019.01)

(58) Field of Classification Search
USPC ....................................... 382/226, 155–160
See application file for complete search history.

(56) References Cited

U.S. PATENT DOCUMENTS 6,636,623 B2 * 10/2003 Nelson ............... G01N 15/1475
382/133
7,542,959 B2 * 6/2009 Barnhill ................. G06Q 20/10
706/48

(Continued)

FOREIGN PATENT DOCUMENTS

| EP | 2229867 A1 | 9/2010 |
| JP | 2007175432 A | 7/2007 |
| WO | 2011135573 A1 | 11/2011 |

OTHER PUBLICATIONS

International Search Report and translation of Written Opinion issued in PCT/EP2019/056295 dated Jun. 12, 2019, 8 pages.

(Continued)

*Primary Examiner* — Timothy J Neal
*Assistant Examiner* — Jae Woo
(74) *Attorney, Agent, or Firm* — Pearne & Gordon LLP

(57) ABSTRACT

The invention relates to a method for producing an image numerical classifier, to automatically determine the visualization quality of endoscopy videocapsule images of segments of the digestive tract, (Continued)

comprising a step of acquiring a video in the digestive tract by a videocapsule; a step of extracting images from the video; a so-called "ground truth" step of clinically evaluating the visualization quality of the images based on medical criteria, a step of selecting an initial set of "adequate" visualization images and "inadequate" visualization images, a step of calculating at least one numerical parameter relating to at least one of the medical criteria, a statistical machine learning step to produce the numerical classifier.

8 Claims, 8 Drawing Sheets

(56) References Cited

U.S. PATENT DOCUMENTS

| | | | | |
|---|---|---|---|---|
| 8,331,699 | B2* | 12/2012 | Dewan | G06K 9/6209 382/226 |
| 8,744,172 | B2* | 6/2014 | Tsymbal | G06F 16/5866 382/159 |
| 8,860,715 | B2* | 10/2014 | Birkbeck | G06K 9/4614 345/419 |
| 8,923,631 | B2* | 12/2014 | Spencer | A61B 8/5223 382/226 |
| 8,983,180 | B2* | 3/2015 | Ko | G06K 9/00335 382/159 |
| 2010/0272358 | A1* | 10/2010 | Kanda | G06T 7/0016 382/173 |
| 2011/0176710 | A1* | 7/2011 | Mattiuzzi | G06T 7/48 382/128 |
| 2016/0048637 | A1 | 2/2016 | Nishiyama | |

OTHER PUBLICATIONS

Goyal, Jatinder, et al. "Analysis of a grading system to assess the quality of small-bowel preparation for capsule endoscopy: in search of the Holy Grail." Endoscopy Int'l Open 2014: 02: E183-E186. 4 pages.

Kohavi, Ron. "A Study of Cross-Validation and Bootstrap for Accuracy Estimation and Model Selection." Proc. of 14th International Joint Conference on Artificial Intelligence (IJCAI), 1995, pp. 1137-1143. 7 pages.

Ladas, S.D., et al. "European Society of Gastrointestinal Endoscopy (ESGE): Recommendations (2009) on clinical use of video capsule endoscopy to investigate small-bowel, esophageal and colonic diseases." Endoscopy 42(3):220-7; 2010 . 8 pages.

McAlindon, Mark E, et al. "Capsule Endoscopy of the small bowel." Annals of Translational Medicine, 4(19): 369; Oct. 4, 2016. 8 pages.

Park, Sung Chul, et al. "A novel cleansing score system for capsule endoscopy." World Journal of Gastroenterology; vol. 16, No. 7, pp. 875-880; Feb. 21, 2010, 6 pages.

Rokkas, et al. "Does Purgative Preparation Influence the Diagnostic Yield of Small Bowel Video Capsule Endoscopy?: A Meta-Analysis." American Journal of Gastroenterology 104(1):219-27; Jan. 2009. 9 pages.

Van Weyenberg, et al. "Description of a novel grading system to assess the quality of bowel preparation in video capsule endoscopy." Endoscopy 43(5): 406-11; Mar. 2011. 7 pages.

* cited by examiner

DEVICE AND METHOD FOR PRODUCING A NUMERICAL CLASSIFIER OF IMAGES, SO AS TO DETERMINE THE VIEWING QUALITY OF THE ENDOSCOPIC VIDEOCAPSULE IMAGES OF A SEGMENT OF THE DIGESTIVE TUBE

FIELD OF THE INVENTION

The present invention relates to a device and a method for determining the visualization quality of images (still images or videos) of endoscopy videocapsule (EVC), of one or more segments of the digestive tract (small bowel, colon, esophagus, or stomach).

STATE OF THE ART

EVC is a first-line method in the exploration of the small bowel, due in particular to its very good safety and tolerance profile (outpatient examination), the fact that the examination is usually complete (in more than 90% of cases), and its good diagnostic cost effectiveness (around 40%, all indications combined) (1).

Since the 2000s, the devices have diversified, important technological advances have emerged. The PillCam SB3® capsule is the 3rd generation capsule of the small bowel from the manufacturer Medtronic. It is the most widespread, but significant competition has emerged, with currently three other EVC systems of the small bowel marketed in France: Mirocam® (Intromedic), Endocapsule® (Olympus), and Capsocam® SV2 (Capsovision). Technological improvements proposed over the last two decades include in particular better image resolution, an increased number of images captured (and possibly adapted to the speed of movement of the capsule in the intestine), an enlarged field of vision, greater energy autonomy, computer aids for the detection and characterization of pathological images. For example, the third-generation SB capsule has an image capture rate of 2 to 6 images per second, higher than that of the second-generation SB.

Despite technological improvements, the cost effectiveness of this examination may be diminished by poor visualization of the mucous membrane due to the presence of food residues, bubbles, or bile in the digestive lumen. Indeed, the capsule has no option for washing or aspiration of the digestive contents, which may interfere with visualization, as is the case in video endoscopy. It was suggested by a meta-analysis including six prospective and six retrospective trials that an intestinal preparation with polyethylene glycol (PEG, 2 to 4 liters the day before) or sodium phosphate provided better visualization of the mucous membrane and better diagnostic performance (2). The recommendations were based on this meta-analysis, recommending the intake of PEG, without formally specifying the volume thereof (3).

Since the drafting of these recommendations, a French multicentric study (PREPINTEST, conducted by the CHU of Brest), randomized 858 patients in 3 arms of different preparation (diet alone, diet with preparation per 2000 ml of PEG the day before, and diet with 500 ml of PEG half an hour after ingestion of the capsule). The cost effectiveness of the examination was of the order of 40% in the 3 groups, but the scores of visualization quality of the mucous membrane were significantly improved by taking PEG (regardless of the modalities). The transit time of the capsule in the intestine was significantly reduced by taking PEG (regardless of the modalities). Taking PEG during an EVC of the small bowel does not have a demonstrated effect on the cost-effectiveness of the test, but appears to improve the reading conditions and the degree of confidence with which an operator will report his/her test conclusions.

One of the major reasons why it is difficult to formally recommend a preparation method of the small bowel, or to conclude in clinical practice on the quality of an examination, is that there is no properly validated score to evaluate the visualization quality of the intestinal mucous membrane, such as the Boston score for the quality of preparation during a colonoscopy.

Such a score is difficult to establish on a clinical basis, because a complete sequence of the small bowel includes thousands of images, some clean, some dirty, in highly variable proportions, with consequently poor reproducibility from one evaluator to another, without a "truth" concerning the visualization quality of an image (and a fortiori of a video sequence) being formally established.

To overcome the difficulty of establishing a "ground truth" in this field concerning the visualization quality of an image of the small bowel, the inventors first considered it important to define what is an adequate visualization quality in order to compare the modalities thereof. By "visualization quality" here is to be understood the ability (for a reader trained in the interpretation of the examination) to see the mucosal surface of the intestine correctly, in particular with respect to its quantity (that is to say the mucosal surface not covered with colored liquids or solid residues or bubbles or any other obstacle) and with respect to its quality (that is to say an examined mucous membrane with correctly rendered colors and adequate brightness—neither too dark nor too overexposed).

Subsequently will be described images with "adequate" visualization (the mucous membrane visualization quality of which is good) and images with "inadequate" visualization (the mucous membrane visualization quality of which is poor).

Evaluation methods have been proposed to conclude that the visualization quality of the examination is acceptable.

These evaluation scales are diverse:

overall qualitative evaluation;

a more detailed qualitative evaluation incorporating the visibility of the mucous membrane, the presence of bubbles or debris, or the darkness of the image (5,6);

quantitative evaluation measuring the percentage of visible mucous membrane, the quantity of bubbles, debris, bile, chyme obstructing the digestive lumen (4,7,8).

One of the most comprehensive, reproducible and easy-to-use scores for EVC of the small bowel is the one proposed by Brotz et al. (4) In this prospective, randomized study, three evaluation scales were compared: an overall qualitative scale (adequate versus inadequate cleanliness), a qualitative scale (poor, moderate, good, excellent cleanliness), and a 10-point quantitative scale, with 5 items between 0 and 2 points (percentage of mucous membrane visualized, abundance of fluids/debris, bubbles, bile/chyme, brightness). There was a strong and significant association between these three scores with better intra- and inter-observer correlation for the quantitative score. While this quantitative score is not formally validated, it is the most widely used.

However, the method is cumbersome to implement as it requires a complete analysis by the practitioner and takes time.

In parallel with the development of clinical scores for the visualization quality of the intestinal mucous membrane during an EVC examination, some authors have proposed an electronic evaluation. Indeed, quality visualization of the images by an examiner is difficult because the whole sequence contains tens of thousands of images. Some authors have therefore developed computer algorithms allowing for an automated and reproducible approach to this question.

Thus, a concept of electronic colorimetric score has been proposed by Van Weyenberg et al. (9) based on the analysis of the red/green pixel ratio of the scroll bar of the SB capsule reading software (Rapid software, Pillcam® system, Medtronic), with a clean series of images being reflected by an area with more red than green in the scroll bar.

This approach was refined at the scale of each individual image in the publication "Development and Validation of a Highly Sensitive and Highly Specific Computed Assessment of Cleansing Score for Small Bowel Capsule Endoscopy" United European Gastroenterology Week. 2016(10). Abou Ali et al. (10) determined and validated a score called ICQPI (Intestinal Preparation Quality Colorimetric Index), based on the red/green ratio (R/G ratio) of still images, with good diagnostic performance (sensitivity at 91%, specificity at 91%) for a ratio>1.6, validated on 2nd generation PillCam® capsules, and with reference to a quadruple reading, blinded, by expert readers.

DISCLOSURE OF THE INVENTION

A purpose of the invention is to provide a method for evaluating the visualization quality of one or more segments of the digestive tract, in particular of the intestinal mucous membrane or colon, during EVC examination.

The invention is based on an automatic analysis by a computer, image by image, which is more efficient and better reproducible than an operator-dependent human evaluation.

To this end, a first aspect of the invention proposes a method of producing an image numerical classifier automatically determining the visualization quality of the endoscopy videocapsule images in at least one segment of a person's digestive tract, comprising the following steps:
  a step of acquiring a video in the segment of the digestive tract by a videocapsule;
  a step of extracting images from the video;
  a so-called "ground truth" step of clinically evaluating the visualization quality of the images by a score, determined by a visual analysis of the images, based on one or more medical criteria,
to distribute these images, depending on the score result:
into so-called "adequate" visualization images and so-called "inadequate" visualization images;
with the medical criteria being selected from the following list: the percentage of mucous membrane visualized, the brightness of the image, the abundance of bubbles, the presence of bile/chyme, the presence of liquids and undigested debris,
  a step of selecting an initial set of images from the so-called "adequate" visualization images and so-called "inadequate" visualization images,
  a step of calculating at least one numerical parameter relating to at least one of the medical criteria of the "ground truth" step, and extracted on each of the images of the initial set;
  a statistical machine learning step comprising:
  a sub-step of selecting learning images from the images of the initial set;
  a sub-step of randomly drawing the learning images;
  a sub-step of automatically producing a numerical classifier, by automatically calculating a distribution function from the one or more calculated numerical parameters,
with the numerical classifier being determined to automatically distribute, at the end of the sub-step, the learning images of the initial set into:
  a first subgroup of learning images with the largest number of so-called "adequate" visualization images, and
  a second subgroup of learning images with the largest number of so-called "inadequate" visualization images.

The "ground truth" step can be replaced by a step of accessing a database already consisting of a set of images distributed into so-called "adequate" visualization quality images and so-called "inadequate" visualization quality images, based on one or more medical criteria.

According to Other Characteristics of the Method:
  the numerical parameters are selected from the following list:
    a global colorimetric parameter of the images,
    one or more parameters reflecting the abundance of bubbles in the images,
    a parameter reflecting the brightness of the image which is the gray-level contrast of the images.
  the global colorimetric parameter of the image is the red/green ratio of the image when the digestive segment is the small bowel; or the red/(green+blue) ratio when the digestive segment is the colon;
  the parameter reflecting the abundance of bubbles is:
    a textural parameter from the gray-level co-occurrence matrix (GLCM) of the processed image, or
    a bubble occupying surface
  the parameter reflecting the brightness of the images is the gray-level contrast of the image.
  the three numerical parameters are calculated in the calculation step, and the sub-step of automatically producing the numerical classifier is performed with the three numerical parameters.
  the sub-step of automatically producing a numerical classifier is repeated several times to obtain several numerical classifiers.
  after the statistical machine learning step are performed:
    a step of numerically testing, using the one or more classifiers learned automatically, so-called "test" images, which are the remaining images of the initial set of images minus the learning images, in the one or more numerical classifiers, and
    a step of numerically deciding the visualization quality of each test image, performed by the one or more classifiers.
  after the statistical machine learning step are performed:
    a step of numerically testing, using the one or more classifiers learned automatically, so-called "test" images, which are the remaining images of the initial set of images minus the learning images, in the one or more numerical classifiers, and
    a step of numerically deciding the visualization quality of each test image, performed by the one or more classifiers.
  the distribution function is a succession of automatic thresholds applied to the one or more calculated numerical parameters,
  the sub-step of producing the classifier is divided as follows according to the technique known as "random forests":

several random draws with delivery of a same number of learning images are performed, from the subset of learning images;

a numerical analysis of these learning images to construct N binary decision trees, a binary decision tree per random draw, with each binary decision tree being constructed using at least one of the numerical parameters, with the resulting set of binary decision trees constituting the numerical classifier, the test image visualization quality decision step is a system for voting on all decisions of the binary decision trees, with each test image having been tested in all binary decision trees.

the sub-step of automatically producing the numerical classifier is performed with at least two numerical parameters;

the automatic thresholds are calculated automatically at each node (level or division point) of each binary decision tree with the numerical parameter that allows the images to be distributed into "adequate" visualization images and "inadequate" visualization images closest to the distribution of "adequate" visualization images and "inadequate" visualization images performed during the "ground truth" step.

the sub-step of automatically producing the numerical classifier is repeated x times to obtain a classifier consisting of all the numerical classifiers resulting from the learning step and thus having x*N binary decision trees, with N greater than or equal to 100 and x greater than or equal to 10.

the sub-step of producing the numerical classifier is performed with a technique selected from the following list:

support vector machine;

binary decision trees in boosting strategy;

neural network.

According to another aspect, the invention relates to a device for producing an image numerical classifier, to determine the visualization quality of endoscopy videocapsule images of a segment of the digestive tract, comprising:

a videocapsule for acquiring a video of segments of the digestive tract by a videocapsule;

image storage means, coupled to the videocapsule;

a database with images extracted from videocapsules and classified: into so-called "adequate" visualization images and so-called "inadequate" visualization images;

processing and calculation means connected to the storage means and incorporating the database, and configured to:

calculating at least one numerical parameter, relating to at least one of the medical criteria, and extracted from the images of the database, with the medical criterion being selected from the following list: the percentage of mucous membrane visualized, the brightness of the image, the presence of bubbles, the presence of bile/chyme, the presence of liquids and undigested debris, perform a statistical machine learning by:

a) randomly drawing the so-called learning images, with the so-called learning images being selected from the images of the database;

b) automatically producing a numerical classifier, by automatically calculating a distribution function from the one or more calculated numerical parameters, with the numerical classifier being determined to automatically distribute, at the end of the sub-step, the learning images into a first subgroup of learning images including the largest number of so-called "adequate" visualization images and a second subgroup of learning images including the largest number of so-called "inadequate" visualization images.

In particular, the device for producing an image numerical classifier, to determine the visualization quality of endoscopy videocapsule images of a segment of the digestive tract, comprises:

a videocapsule for acquiring a video of segments of the digestive tract;

image storage means, coupled to the videocapsule;

a database with videocapsule-extracted images classified during a ground truth step: into so-called "adequate" visualization images and so-called "inadequate" visualization images; according to a score, determined by a visual analysis of the images, based on one or more medical criteria, with the medical criterion being selected from the following list: the percentage of mucous membrane visualized, the brightness of the image, the presence of bubbles, the presence of bile/chyme, the presence of liquids and undigested debris, processing and calculation means connected to the storage means and incorporating the database, and configured to:

calculate at least two numerical parameters, each relating to at least one of the medical criteria of the score, and extracted from the images of the database, perform a statistical machine learning according to the technique known as "random forests" which has:

a) several sub-steps of random drawing with delivery of a same number of learning images which is a subset of images of the database;

b) a sub-step of automatically producing the classifier, with a succession of automatic thresholds applied to the calculated numerical parameters, by numerical analysis of these learning images to construct N binary decision trees, with one binary decision tree per random draw, with each binary decision tree being constructed using at least the two numerical parameters, with the automatic thresholds being calculated automatically, at each node of each binary decision tree, with the numerical parameter that allows for the distribution of the learning images into a first subgroup and into a second subgroup closest to the distribution of the so-called "adequate" visualization images and so-called "inadequate visualization images performed during a "ground truth" step, with the resulting set of binary decision trees constituting the numerical classifier, with the numerical classifier being determined to automatically distribute, at the end of sub-step b), the learning images into a first subgroup of learning images including the largest number of so-called "adequate" visualization images and a second subgroup of learning images including the largest number of so-called "inadequate" visualization images, wherein the one or more numerical parameter are selected from the following list:

a global colorimetric parameter of the images, one or more parameters reflecting the abundance of bubbles in the images, a parameter reflecting the brightness of the image which is the gray-level contrast of the images.

According to Other Features of the Invention, in the Device According to the Invention:

the sub-step of automatically producing the numerical classifier is performed with the three following numerical parameters:
the global colorimetric parameter of the image is the red/green ratio of the image when the digestive segment is the small bowel; or the red/(green+blue) ratio when the digestive segment is the colon;
the parameter reflecting the abundance of bubbles is:
a textural parameter from the gray-level co-occurrence matrix (GLCM) of the processed image, or
a bubble occupying surface
the parameter reflecting the brightness of the images is the gray-level contrast of the image.
the processing and calculation means are configured to:
produce the numerical classifier according to the technique known as "random forests" which has:
several sub-steps of random drawing with delivery of a same number of learning images, from the subset of learning images;
a sub-step of numerically analyzing these learning images to construct N binary decision trees,
a binary decision tree per random draw,
with each binary decision tree being constructed using at least one of the numerical parameters,
with the resulting set of binary decision trees constituting the numerical classifier,
perform a test image visualization quality numerical decision step, which is a system for voting on all digital decisions of the binary decision trees, with each test image having been tested in all binary decision trees.

According to a third aspect, the invention relates to a control method applied to a video made by a videocapsule, of at least one segment of a person's digestive tract, to automatically determine the visualization quality of the images of the video, using the image numerical classifier produced by the method according to the invention, applied to the images in the video, to automatically determine, in an automatic control examination, the images with "adequate" visualization, the images with "inadequate" visualization, and the rate of "adequate" visualization images in the video according to the decision of the numerical classifier. According to another feature of the invention, the method has:
a preliminary step of intestinal preparation for the control examination, different for each person;
an automatic examination control step,
a step of comparing the efficacy of the different intestinal preparations under examination depending on the rate of "adequate" visualization images determined for each different intestinal preparation by the control method.

According to a fourth aspect, the invention provides a control device for automatically determining the visualization quality of a video of one or more segments of a person's digestive tract, performed by an endoscopy videocapsule, comprising:
a videocapsule for acquiring a video of at least one segment of a digestive tract;
image storage means coupled to the videocapsule;
processing and calculation means connected to the storage means and incorporating the numerical classifier produced by the method defined according to the invention,
and configured to:
calculate at least one numerical parameter relating to at least one of the medical criteria, in the images of the video,
with the medical criterion being selected from the following list: the percentage of mucous membrane visualized, the brightness of the image, the presence of bubbles, the presence of bile/chyme, the presence of liquids and undigested debris,
numerically test the images in the video, and numerically decide the images with "adequate" visualization, the images with "inadequate" visualization, and the rate of "adequate" visualization images in the video according to the decision of the numerical classifier.

DESCRIPTION OF THE FIGURES

Other objectives, features and advantages will become apparent from the following detailed description with reference to the drawings given for illustrative and non-exhaustive purposes, among which.

DETAILED DESCRIPTION OF THE INVENTION

1—Method for Producing a Numerical Classifier

Figure 1:
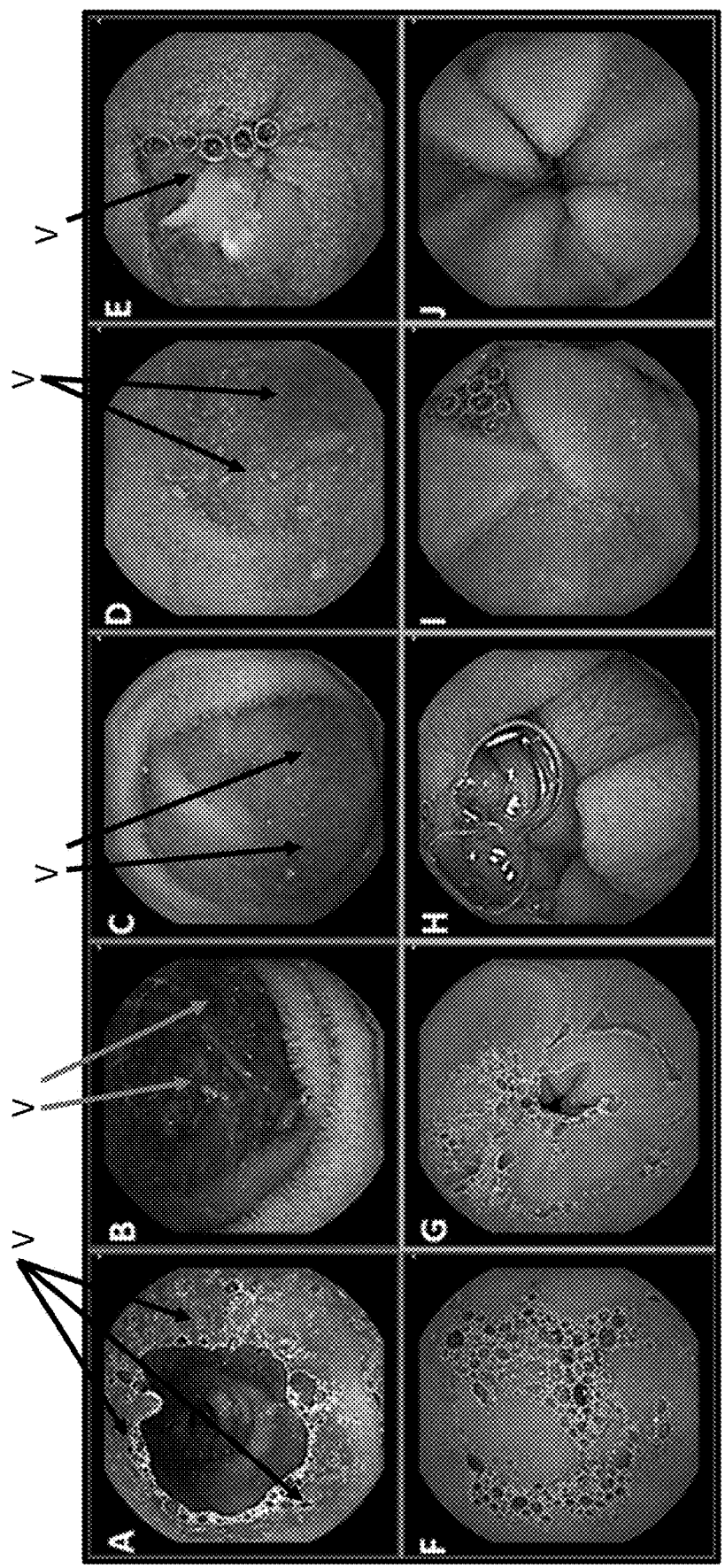
FIG. 1 shows images corresponding to an overall score rating greater than 7 ("clean" image) or <7 ("dirty" image) according to a possible embodiment of the invention.

The present invention relates to a method for producing an image numerical classifier, to automatically determine the visualization quality of endoscopy videocapsule images of one or more segments of the digestive tract.

This producing method has the following steps:
a step of acquiring a video in one or more segments of the digestive tract by a videocapsule;
a step of extracting images from the video;
a so-called "ground truth" step of clinically evaluating the visualization quality of the images based on medical criteria, by determining a score by visual analysis (performed for example by a doctor or a competent person), to distribute these images, according to the result of the score, into at least: so-called "adequate" visualization images and so-called "inadequate" visualization images;
a step of selecting an initial set of images from the so-called "adequate" visualization images and so-called "inadequate" visualization images,
a step of calculating at least one numerical parameter relating to one of the medical criteria of the "ground truth" step, on each of the images;
a statistical machine learning step.

The statistical machine learning step comprises:
a sub-step of selecting learning images from the images of the initial set;
a sub-step of randomly drawing the learning images;
a sub-step of automatically producing a numerical classifier of the learning images, from at least one numerical parameter, and which is produced with or based on:
an automatic calculation of a distribution function from the one or more calculated numerical parameters,
the known distribution of into so-called "adequate" quality images and so-called "inadequate" quality images performed during the "ground truth" step or known from a database.

The distribution function can be binary or in multiple classes.

The medical criteria can be selected from the following list in particular: the percentage of mucous membrane visualized, the brightness of the image, the presence of bubbles, the presence of bile/chyme, the presence of liquids and undigested debris (food, medication, feces, blood, or other)

The segments of the digestive tract can be the small bowel, colon, esophagus, and/or stomach. Advantageously, the automatic learning sub-step can be repeated to obtain several numerical classifiers.

Then the method includes:
a step of numerically testing each so-called "test" image (the "test" images are the remaining images of the initial set of images minus the learning images), in the one or more classifiers developed in the statistical machine learning step, and
a step of numerically deciding the visualization quality of the test image performed by the one or more classifiers from the learning step,
allowing to quantify performance (e.g. to determine sensitivity and specificity).

Advantageously, the image extraction step is carried out from videos of several people. For example, several hundred or thousand images are used as an initial set of images E (e.g. 600), a so-called "large" subset F of several hundreds or thousands of learning images (e.g. 500), and a so-called "small" subset G of test images with G=E-F (e.g. 100).

In the selection step, as many learning images (e.g. 300) as test images (e.g. 300) were taken.

This method may be generalized to the esophagus, stomach, small bowel, and/or colon, individually or in combination (in particular small bowel and colon), with the use of endoscopy videocapsules adapted to one or more segments of the digestive tract, as appropriate.

Similarly, it is possible to use panenteric capsules that cover the entire length of the digestive tract.

The electronic analyses of visualization quality can be carried out online on the Internet; the videos can be sent to servers, analyzed online, and then the reports sent back to the doctor.

The one or more numeric parameters are selected from the following list:
an overall colorimetric parameter of the image, which is for example the red/green ratio of the image for the small bowel; or the red/(green+blue) ratio for the colon;
one or more parameters reflecting the abundance of bubbles in the image, such as:
a textural parameter from the gray-level co-occurrence matrix (GLCM) of the processed image, or
a bubble occupying surface
a parameter reflecting the brightness of the image which is the gray-level contrast of the image (contrast as defined by Haralick [1974]).

Advantageously, the sub-step of automatically producing the numerical classifier is performed with the 3 numerical parameters.

Advantageously, the one or more numerical parameters are selected so that the method has a minimum sensitivity (number of so-called "adequate" visualization quality images selected by the learning step/total number of so-called "adequate" quality images) of 90% and a minimum specificity (number of "inadequate" visualization quality images selected by the learning step/total number of "inadequate" visualization quality images according to the ground truth) of 70% desired.

The present invention also relates to a device for producing an image numerical classifier, to automatically determine the visualization quality of endoscopy videocapsule images of the small bowel or colon, comprising:
a videocapsule for acquiring the images of the digestive tract by a videocapsule;
image storage means, coupled to the videocapsule;
a database with images extracted from videocapsules and classified: into so-called "adequate" visualization images and so-called "inadequate" visualization images;
processing and calculation means connected to the storage means and incorporating the database.

These processing and calculation means are configured to:
calculate at least one numerical parameter relating to at least one of the medical criteria in the images of the database, and mentioned above,
perform a statistical machine learning by:
a) randomly drawing the so-called learning images, with the so-called learning images being selected from the images of the database;
b) automatically producing a numerical classifier from at least one calculated numerical parameter, which is produced with:
an automatic definition of the automatic thresholds in relation to the calculated numerical parameter,
the classification (or distribution) of the images into "adequate" and "inadequate" images.

1.1) Technique Known as "Random Forests"

In the case where the function is binary, the distribution function consists of a succession of automatic thresholds, and for each threshold "stage", the numerical parameter which allows for the best distribution of the images and the associated automatic threshold is determined, with this numerical parameter being selected (which may be different) at each "stage" in the succession of automatic thresholds to optimize the distribution of the images.

Thus, the automatic thresholds are determined to automatically distribute, at the end of the learning sub-step, the learning images into two subgroups, with a first subgroup of learning images having to include the largest number of so-called "adequate" visualization images and a second subgroup of learning images having to include the largest number of so-called "inadequate" visualization images.

In other words, the construction of the classifier is characterized by an automatic, iterative, and dichotomous calculation of thresholds associated with the numerical parameters extracted from the learning images, to numerically distribute the images into numerically classified images: in "adequate" quality, or in "inadequate" quality.

The thresholds are determined automatically in the learning step to minimize the error of classification (or distribution) of numerically classified (in "adequate" or "inadequate" quality) images, with the clinicians' ground truth being used here as a reference in order to calculate the error associated with a choice of threshold.

The thus automatically learned thresholds are called final thresholds and are then used in the testing step to numerically classify so-called "test" images and determine the sensitivity and selectivity [always in relation to the images with the clinicians' reference distribution (in "adequate" and "inadequate" quality)] of the method.

More specifically, the so-called "random forest" technique is divided as follows:

several random draws with delivery of a same number of learning images are performed, from the subset of learning images;

a numerical analysis of these learning images to construct N binary decision trees, one binary decision tree per random draw, with each binary decision tree being constructed using at least one of the numerical parameters, and presenting at the end of the learning step automatic thresholds calculated as a function of the numerical parameters with the resulting set of binary decision trees constituting the numerical classifier.

Decision trees are classification or distribution tools belonging to the category of so-called recursive partitioning methods. All the observations are grouped at the root of the tree, and then each division or cut separates each node into two son nodes more homogeneous than the father node according to a criterion to be specified. In this case, the R/G, GLCM, brightness parameters calculated on each learning image constitute an observation batch (explanatory variables) characterized by a ground truth (adequate/inadequate visualization).

Figure 7:
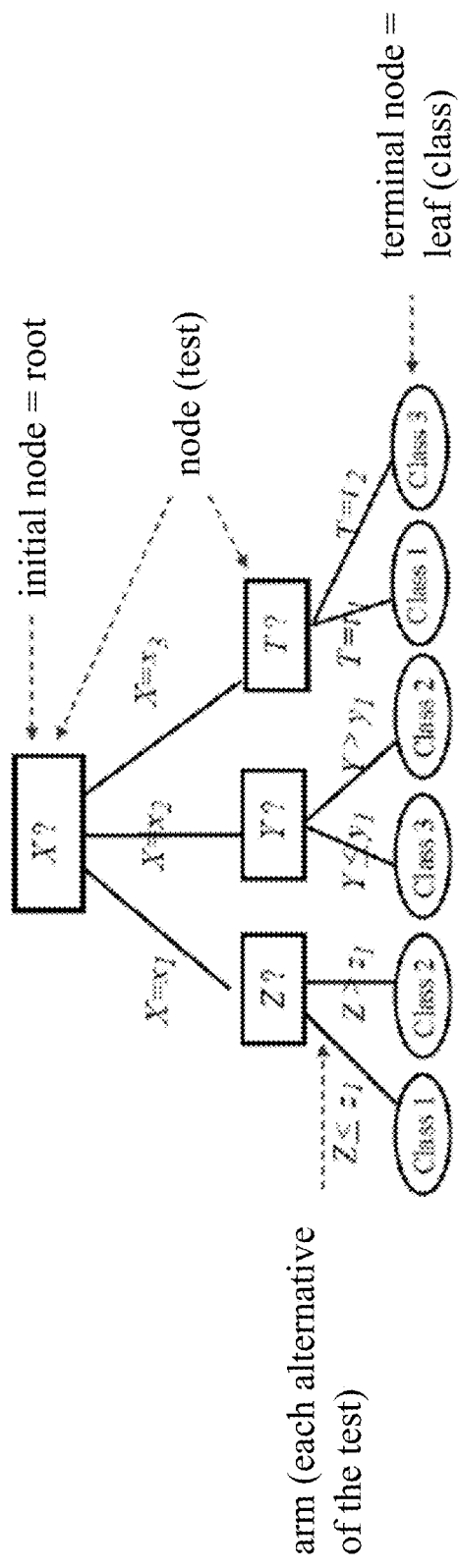
FIG. 7 shows the explanation of the so-called random forest method.

The construction of a binary discrimination tree (see FIG. 7) from these quantitative observations consists in determining a sequence of nodes:

A node is defined by the joint choice of an explanatory variable and a division that induces a partition into two classes. Implicitly, to each node thus corresponds a subset of the observation sample to which a dichotomy is applied.

A division is itself defined by a threshold value of the selected quantitative explanatory variable. Preferably, corresponding here to one of the numerical parameters relating to the medical criteria, and to each node, is associated, to calculate the threshold, one numerical parameter rather than another, so that the successive divisions related to each successive node allow to converge towards the best possible classification of the images for each binary decision tree (at the level of the terminal nodes).

The root or initial node corresponds to the entire sample; the procedure is then iterated over each of the subsets.

The algorithm requires:

The definition of a criterion for selecting the best division among all those admissible for the different variables or numerical parameters (a division is said to be admissible if neither of the two resulting descending nodes are empty);

A rule for deciding that a node is terminal: it then becomes a leaf;

The assignment of each leaf to one of the classes or to a value of the variable to be explained (adequate/inadequate visualization here).

An advantage of the present invention is to calculate the threshold at each node of the tree with respect to one of the numerical parameters (each relating to at least one of the medical criteria of the score), which is selected for each node of the tree to optimize the classification of the images at the level of the end nodes or leaves and to make it tend (after successive use of several binary decision trees) as much as possible towards the classification produced by the experts known as the ground truth.

The homogeneity criterion for selecting the best division among those admissible is in this case an entropic criterion for giving a measure of the gain in classification or distribution between two levels of the tree (Gini index, Shannon entropy).

A set of binary decision trees constructed on subsets from the learning images forms a forest. The test image visualization quality decision step can be a system for voting on all decisions of the binary decision trees, with each test image having been tested in all binary decision trees.

1.2) Multi-Class Distribution Function

In the case where the distribution function is a multi-class function (number of classes>2), in another embodiment of the invention, the sub-step of producing the numerical classifier is performed with a technique selected from the following list:

support vector machine;

neural network.

binary decision trees in boosting strategy.

Boosting is an area of automatic learning (branch of the artificial intelligence). It is a principle that brings together many algorithms based on sets of binary classifiers: boosting optimizes their performance.

2—Control Method

The present invention also relates to a control method applied to a series of successive images (video) taken by digestive videocapsule (in the small bowel, colon, stomach, and/or esophagus) of a person, to numerically determine the visualization quality of the images of the video, using the image numerical classifier produced by the method defined above, applied to the images in the video, to numerically determine the images with "adequate" visualization, the images with "inadequate" visualization, and the "adequate" frame rate in the video based on the result of the numerical classifier.

In this case:

a step of numerically testing the numerical classifier with the final thresholds is performed directly on the images of the video, and a step of numerically deciding the visualization quality is performed directly on the images of the video.

It is thus possible:

to objectively measure the effectiveness of bowel preparation modalities under examination (e.g. diets, laxative solutions, or anti-bubble agents);

to objectively compare the effectiveness of different bowel preparation modalities (e.g. diets, laxative solutions, or anti-bubble agents);

to describe a correct bowel visualization quality level by videocapsule, with a sufficient proportion of images with "adequate" visualization quality (e.g. more than 80% of the images with visualization quality) for concluding that a videocapsule examination is "clean" and "reliable", and if not, to repeat the examination.

Validated bowel preparation protocols will improve the quality of care by avoiding the repetition of several videocapsules for the same patient due to inadequate bowel preparation and visualization.

The present invention also relates to a control device for numerically and automatically determining the quality of visualization of a video of the small bowel, colon, stomach, and/or esophagus of a person, performed by endoscopy videocapsule, comprising:

a videocapsule for acquiring a video of one or more digestive segments of the digestive tract;

image storage means coupled to the videocapsule;

processing and calculation means connected to the storage means and incorporating the numerical classifier produced by the method defined above in the description, The processing and calculation means are configured to:

Calculate at least one numerical parameter relating to at least one of the medical criteria, in the images of the video, Numerically test the images of the video, and numerically decide on the visualization quality of the images of the video, with the numerical classifier produced according to the method defined above in the description.

Experimental Part

The main objective of the method of the invention is to evaluate the diagnostic performances, isolated and then combined, of 3 methods of electronic analysis of the visualization quality of the mucous membrane of fixed images of 3rd generation small bowel EVCs:

the analysis of the red/green pixel ratio in the image;

an index reflecting the abundance of bubbles, based on a gray-level co-occurrence matrix (GLCM);

an index reflecting the brightness.

It was first hypothesized that in an electronic analysis of EVC images, combining the "colorimetry" and "bubble detection" approaches could be more efficient than using each approach in isolation. In addition, apart from colorimetry (red/green ratio, reflecting the visualization of the pink mucous membrane, and the presence of bile and greenish residues) and the quantity of bubbles (10% threshold), the other items of the Brotz et al. score (4) (especially the brightness) are not integrated into electronic image analysis. It was then hypothesized that optionally integrating an additional parameter reflecting the degree of brightness of the EVC images could further improve their electronic analysis for the evaluation of the mucous membrane visualization quality.

The results are conclusive.

The secondary objective was to determine the time required for the analysis of an image according to the method of the invention.

Material and Methods

Patient and Image Selection

Thirty complete, normal endoscopy small bowel videocapsules of the Pillcam SB3® (Medtronic) type were selected. These examinations were all carried out in the same hospital center, after a standardized preparation prescribed to the patient. They were read by the same practitioner. The indication was the same for all the tests: unexplained digestive bleeding. All videocapsules had to be complete (that is to say the entire small bowel was seen), and normal (no pathological images were seen, and no trace of blood was observed). The overall preparation of the EVC was rated as "good", "fairly good", or "average".

The videos were anonymized. The video sequences corresponding strictly to the small bowel (from the first to the last image of the small bowel) were extracted and transformed into a universal format (mpeg) using RAPID® (Medtronic) reader software.

Six hundred still images were randomly extracted and transformed into a universal format (jpeg), for electronic analysis in a second step.

These images were read by three experts in reading endoscopy videocapsules of the small bowel. The experts evaluated the 600 images independently, without the interpretation of other readers, and without the knowledge of any electronic analysis. The experts rated the image quality of each of the 600 images according to the quantitative index grid of Brotz et al. (4). Five criteria were evaluated:

the percentage of mucous membrane visualized (<80%, 80 to 90%, >90%, giving 0, 1, or 2 points, respectively), the brightness of the image (high noted at 0 point, moderate at 1 point, and low at 2 points), the presence of bubbles (high noted at 0 point, moderate at 1 point, and low at 2 points), the presence of bile/chyme (high noted at 0 point, moderate at 1 point, and low at 2 points), the presence of liquids and debris (high, moderate, or low, giving 0, 1, or 2 points, respectively).

The score therefore varied between 0 and 10. The average of the three ratings constituted the "ground truth" (groundtruth) and was used as a reference for the evaluation of the electronic indices.

The distribution curves of the quantitative score in the paper by Brotz et al. (4) were examined. It appeared that the vast majority of the sequences considered "clean" in this study had a quantitative score greater than or equal to 7. As a result, any image from the bank, the average quantitative score of which was greater than or equal to 7 out of 10 was considered to have "good" visualization quality. Conversely, any image, the average quantitative score of which was strictly less than 7 out of 10, was considered to have "poor" visualization quality.

By extrapolation, for each sub-score corresponding to each of the 5 criteria, it was considered that the analysis was "good" for a value greater than or equal to 1.4 out of 2.

These images were analyzed electronically according to the three above-mentioned parameters (red/green pixel ratio, abundance of bubbles, brightness). The result of the electronic analysis was compared with that of the expert reading, in terms of sensitivity and specificity, for the three electronic criteria, individually, and in combination with each other.

Electronic Analysis and Statistics

The 600 images were analyzed electronically at the École Nationale Supérieure de l'Électronique et de ses Applications (ENSEA, Cergy) using MATLAB® software. For each image were measured:

the red/green pixel ratio, the presence of bubbles using a gray-level co-occurrence matrix (GLCM), the brightness or contrast of the image.

1—Learning Step

A first step of electronic analysis of the images, known as learning, used a base consisting of 500 images drawn at random among the 600 selected with the "ground truth" established by the expert readers as a reference, to train the statistical classifier in question. The selected classifier was developed using a method called decision tree forests (also called random forests) (11). This type of decision support tool is widely used in the field of learning-based data analysis.

These decision trees describe how to classify or distribute a complex data set (such as a population or, here, a series of images) according to a set of discriminating variables (here red/green ratio, co-occurrence matrix, brightness) and according to a goal set in terms of number of classes (here "good" or "poor" visualization quality images) based on a ground truth (here the average scores of the experts). In order to ensure a better stability of the performance of this type of algorithm (sensitive to the learning database), decision tree forests perform learning on multiple decision trees trained on slightly different subsets of data created on the basis of the 500 images considered.

2—Test Step

A second step allowed to test the performance of the first learning.

Here, the test base consisted of 100 images drawn at random from the 600 selected images, with the ground truth established by the expert readers as a reference. These images were classified by the previously learned classifier. It was then possible to deduce the performance of the classifier.

3—Measurement of Classifier Performance by "Cross-Validation"

In order to obtain performance that was statistically representative of and not dependent on the draw of the learning and testing and validation bases, a "cross-validation" method was used to evaluate the diagnostic performance of the different criteria tested (red/green ratio, bubbles, brightness, and their combinations). This method of cross-validation, which has been proven in the field of electronic image analysis, was based on the following principle: an initial learning was carried out on 500 randomly selected images out of the 600, and then validation was carried out on the remaining 100 images; the operation was repeated ten times. The diagnostic performances (sensitivity, specificity) of the method were then characterized by the average ROC curve obtained over the 10 draws (12).

Judgment Criteria

The criterion for primary judgment was the sensitivity and specificity of the combination of the three criteria tested (R/G ratio, GLCM, brightness).

The criteria for secondary judgment were: the sensitivity and specificity of each of the individual criteria.

The time required for the electronic analysis of an image thanks to the 3 tested criteria (red/green pixel ratio, co-occurrence matrix contrast in gray levels a brightness index) was also tested.

Results

A) Expert Analysis

A1) Quantitative Analysis

The average ratings (out of 2 points) given for each of the criteria by the 3 expert readers are reported in Tables 2 to 6. Ratings were below the threshold of 1.4 out of 2 in 72% of the images for the criterion "percentage of mucous membrane visualized" (Table 2), 65% for the criterion "debris, residues, liquids" (Table 3), 67% for the criterion "bubble" (Table 4), 61% for the criterion "bile/chyme" (Table 5), and 47% for the criterion "brightness" (Table 6). The overall rating was greater than or equal to 7 out of 10, and therefore allowed the image to be distributed as having "good" quality, for 40.5% of the images for reader 1, 37% of the images for reader 2, and 39% for reader 3, with an average of 37% for all 3 readers (Table 7).

Examples of "good" and "poor" preparation quality images are shown in FIG. 1. The places which are green (presence of bile) in the photos were indicated by arrows V.

A2) Inter-Observer Correlation

The kappa coefficients of inter-observer correlation are shown in Table 8 regarding the overall rating, determining the cleanliness of an image (rating Agreement on the analysis of the three experts was good to excellent, with the kappa coefficient of reader 1 with reader 2 and reader 3 being 0.83 and 0.81, respectively. It was 0.87 between reader 2 and reader 3.

B) Electronic Analysis

B1) Diagnostic Performance

The 600 images were analyzed using previously validated algorithms (the red/green pixel ratio, a contrast evaluation method derived from the co-occurrence matrix, where the contrast of the image is similar to the brightness thereof), and compared with the reading of the three experts, having determined that the threshold beyond which an image was of good visualization quality had an overall rating greater than or equal to 7 out of 10.

Figure 2:
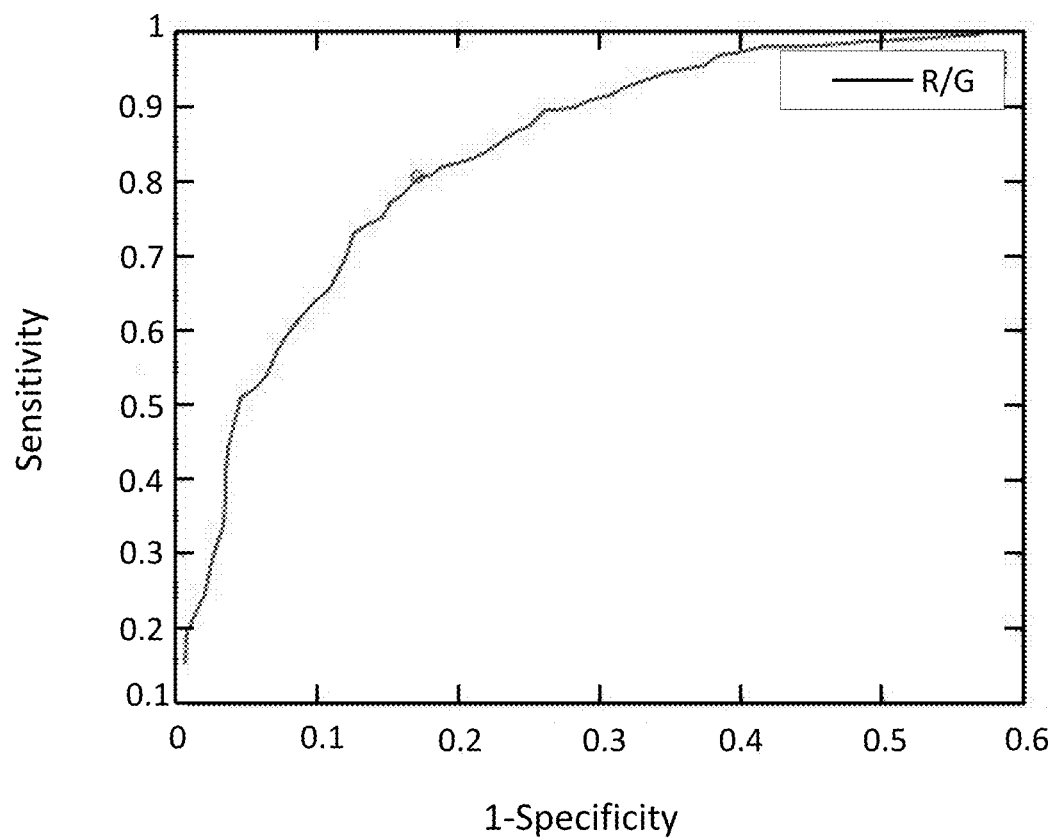
FIG. 2 shows the ROC curve obtained with the method according to the invention for the red/green pixel ratio parameter.

As regards the red/green pixel ratio criterion, the sensitivity was 80% and the specificity 83% (FIG. 2).

Figure 4:
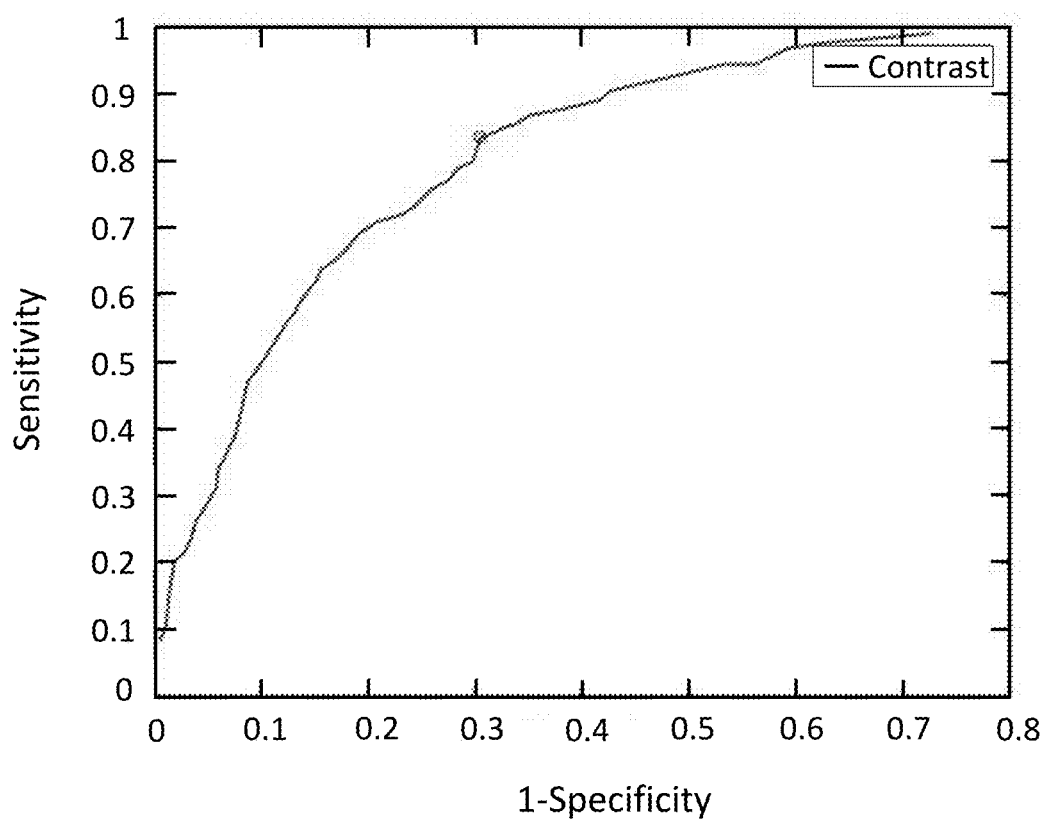
FIG. 4 shows the ROC curve obtained with the method according to the invention for the brightness parameter.
Figure 5:
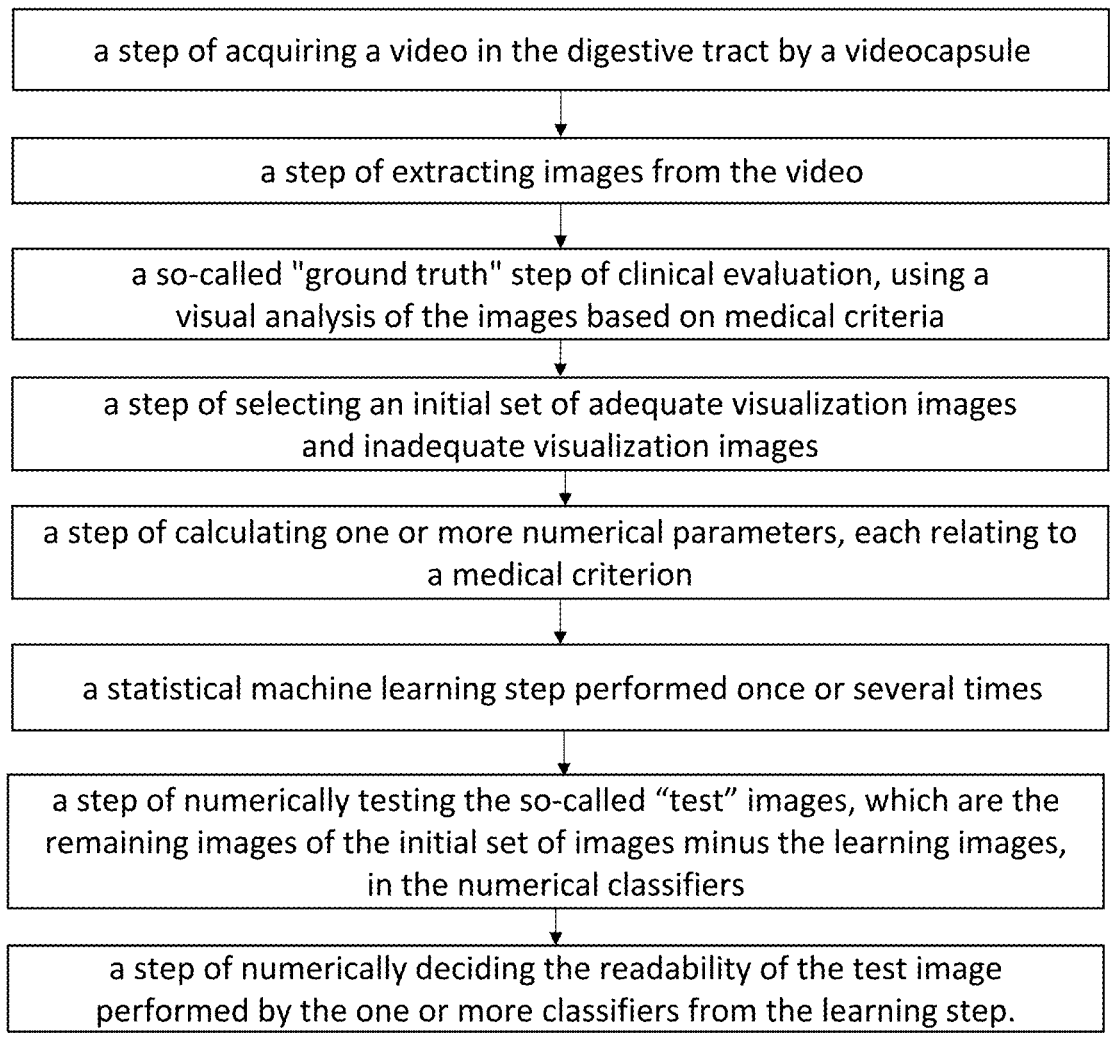
FIG. 5 shows the method according to the invention.
Figure 6:
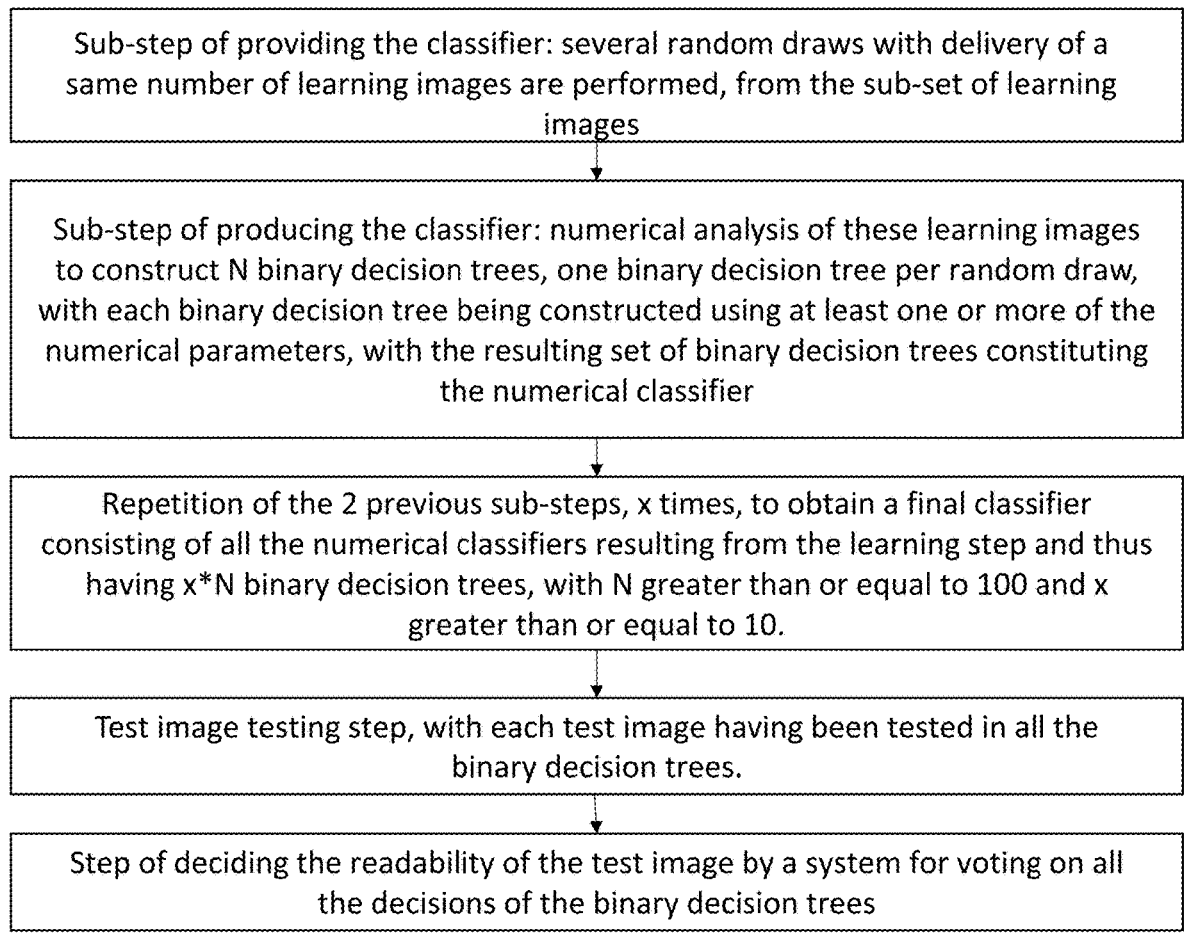
FIG. 6 shows the sub-step of producing the classifier according to one embodiment of the invention.

For the contrast of a gray-level co-occurrence matrix, the sensitivity and specificity were 84% and 70%, respectively (FIG. 4).

Figure 3:
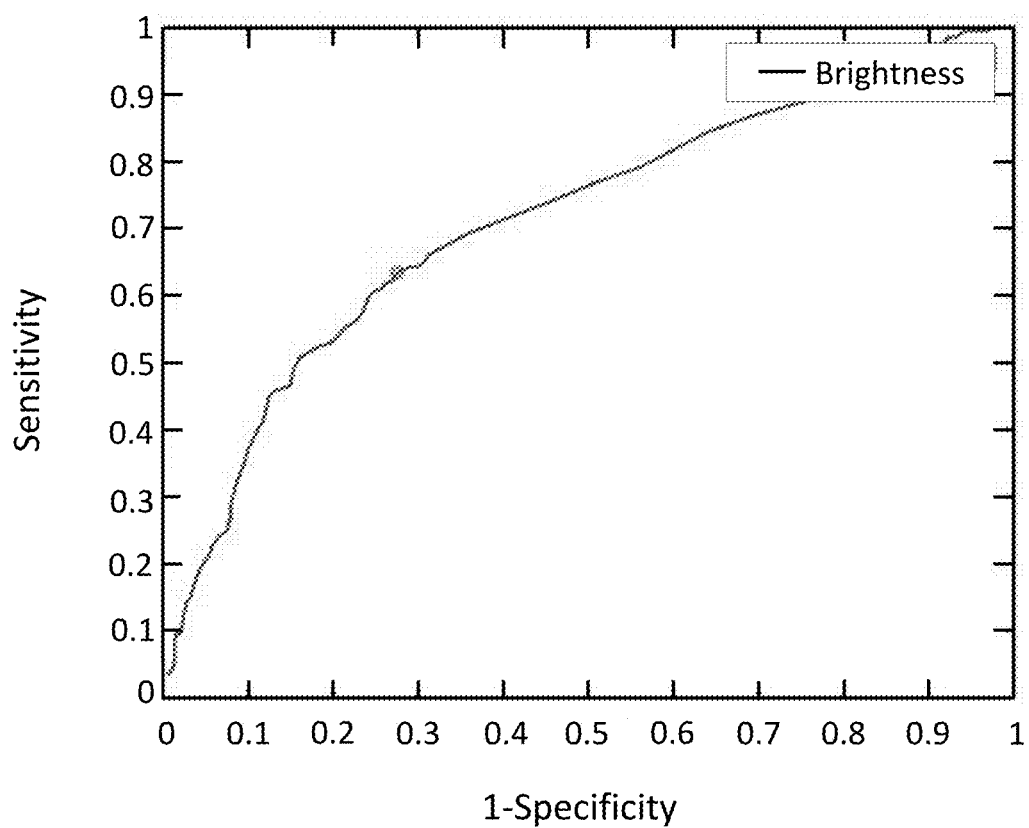
FIG. 3 shows the ROC curve obtained with the method according to the invention for the GLCM parameter.

For the brightness, sensitivity was 62% and specificity 74% (FIG. 3).

Figure 8:
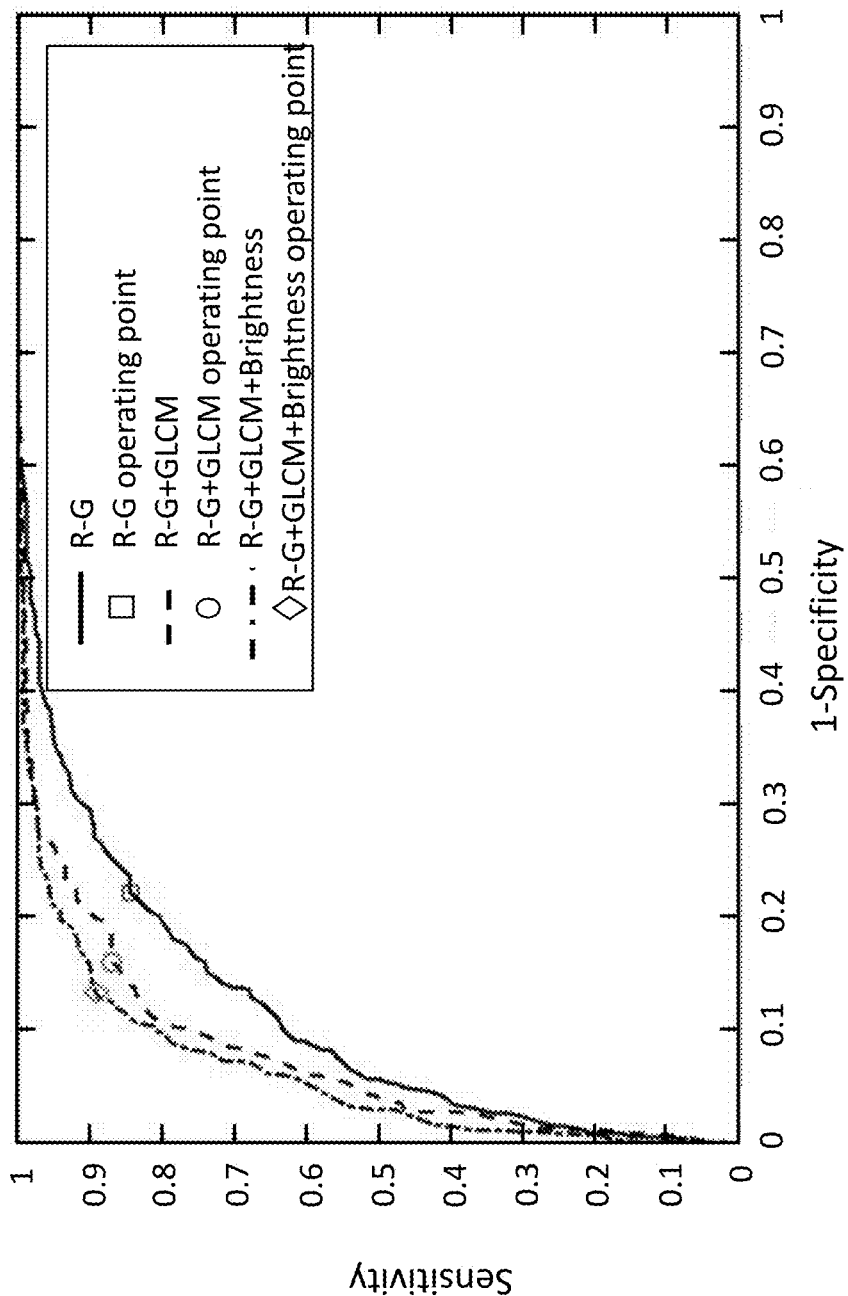
FIG. 8 shows the ROC curves resulting from the method according to the invention highlighting the improvement of the analysis techniques using the 3 parameters.

Using the regression tree method, which allowed a combination of these three criteria, the sensitivity was 90% and the specificity 88% (FIG. 8).

B2) Analysis Time

The time required for the electronic analysis of an image according to the three criteria tested (red/green pixel ratio, gray-level co-occurrence matrix contrast, and brightness index) was 2.3 milliseconds.

B3) Discussion

A composite electronic analysis method has been proposed according to the invention for determining whether a still image of EVC of the small bowel has good visualization quality. This method includes three parameters: the red/green pixel ratio (representing mucous membrane visualization), a gray-level co-occurrence matrix contrast (representing the abundance of bubbles), and a brightness index. The raw combination of these three criteria allows for good diagnostic performance: 90% sensitivity and 88% specificity.

The scale that seems to us to be the most complete, reliable, reproducible, and reliable to conclude on the visualization quality of the images of the examination is the quantitative scale of Brotz et al. (4) that we have relied on here for the expert evaluation. Among the three scores developed by the authors, the quantitative scale is the one with the best reproducibility (compared to the qualitative scale and the global evaluation), yet with moderate intra-observer coefficients (0.60 to 0.66) on video sequences.

Most previous work analyzes the entire examination or video sequences to determine if the visualization quality is satisfactory. Indeed, video analysis can be less accurate because it evaluates sequences of thousands of images, often heterogeneous in terms of visualization quality, thus leading to a less reproducible judgment. In order to obtain a solid ground truth, it was decided to base the work on the evaluation of still images with the aim of integrating it into a computer software, as man cannot, in the long run, analyze images one by one. An electronic analysis independent of the human eye would be objective, fast, perfectly reproducible, and saves a considerable amount of time.

In total, to establish a "ground truth", 600 still images (not sequences containing thousands of images) were therefore considered and the average of the quantitative scores of three experts (not individual scores) was used. This quantitative score, proposed and published by Brotz et al. (4) has been used since its publication in other works. The expert readings were done for each expert without the knowledge of the interpretation of the other readers, and without the knowledge of any electronic analysis.

The work evaluated a very complete score, integrating multiple components qualifying the visualization quality of an image of EVC of the small bowel: the percentage of mucous membrane visualized, the abundance of bubbles, the presence of bile, residues, debris, and brightness. The "ground truth" is based on a strong agreement between the analysis of the three experts, with the kappa coefficients ranging from 0.81 to 0.87 for the overall rating.

The strong points are that a large and varied image database was evaluated, that our results are based on a solid "ground truth" with strong inter-observer agreements. This work is based on an electronic analysis, and therefore objective, reproducible, which could eventually, if it leads to a validated score, be integrated into EVC reading software. The work, which is original, is the first to offer such a complete score, taking into account multiple quality criteria for evaluating the visualization quality of EVC images of the small bowel.

CONCLUSION

A multi-criteria electronic evaluation method integrating the analysis of a red/green pixel ratio, the abundance of bubbles, and image brightness is proposed to determine the visualization quality of 3rd generation small bowel EVC images. This composite score is reliable, easy to use, reproducible, and could be integrated with reading software to facilitate the determination of the visualization quality of EVC images and thus conclude on the level of reliability of each examination. It could also provide a reproducible comparison of the different preparation methods to validate the procedure to be followed and the recommendations.

Tables

TABLE 1

Image Evaluation Grid

| Points | % of mucous membrane visualized | Amount of debris/residue/fluid | Quantity of bubbles | Quantity of chyme/bile | Brightness reduction |
|---|---|---|---|---|---|
| 0 | <80% | high | high | high | high |
| 1 | 80-89% | moderate | moderate | moderate | moderate |
| 2 | >=90% | minimal/low | minimal/low | minimal/low | minimal/low |

TABLE 2

Expert ratings for the criterion "Percentage of mucous membrane visualized"

| | Ratings | | | Average | |
|---|---|---|---|---|---|
| | Nb images at 0 | Nb images at 1 | Nb images at 2 | <1.4 (%) | ≥1.4 (%) |
| Reader 1 | 293 (49%) | 131 (22%) | 176 (29%) | | |
| Reader 2 | 347 (58%) | 94 (15.5%) | 159 (26.5%) | | |
| Reader 3 | 328 (54.5%) | 88 (14.5%) | 184 (31%) | | |
| 3 readers | | | | 431 (72%) | 169 (28%) |

TABLE 3

Expert ratings for the criterion "Debris, residues, fluids"

| | Ratings | | | Average | |
|---|---|---|---|---|---|
| | Nb images at 0 | Nb images at 1 | Nb images at 2 | <1.4 (%) | ≥1.4 (%) |
| Reader 1 | 142 (23.5%) | 132 (22%) | 326 (54.5%) | | |
| Reader 2 | 253 (42%) | 159 (26.5%) | 188 (31.5%) | | |
| Reader 3 | 186 (31%) | 123 (20.5%) | 291 (48.5%) | | |
| 3 readers | | | | 388 (65%) | 212 (35%) |

TABLE 4

Expert ratings for the criterion "Bubbles"

| | Ratings | | | Average | |
|---|---|---|---|---|---|
| | Nb images at 0 | Nb images at 1 | Nb images at 2 | <1.4 (%) | ≥1.4 (%) |
| Reader 1 | 261 (43.5%) | 110 (18.5%) | 229 (38%) | | |
| Reader 2 | 234 (39%) | 97 (16%) | 269 (45%) | | |
| Reader 3 | 133 (22%) | 206 (34.5%) | 261 (43.5%) | | |
| 3 readers | | | | 401 (67%) | 199 (33%) |

TABLE 5

Expert ratings for the criterion "Bile/Chyme"

| | Ratings | | | Average | |
|---|---|---|---|---|---|
| | Nb images at 0 | Nb images at 1 | Nb images at 2 | <1.4 (%) | ≥1.4 (%) |
| Reader 1 | 114 (19%) | 209 (35%) | 277 (46%) | | |
| Reader 2 | 249 (41.5%) | 115 (19%) | 236 (39.5%) | | |
| Reader 3 | 189 (31.5%) | 155 (26%) | 256 (42.5%) | | |
| 3 readers | | | | 364 (61%) | 236 (39%) |

TABLE 6

Expert ratings for the criterion "Brightness"

| | Ratings | | | Average | |
|---|---|---|---|---|---|
| | Nb images at 0 | Nb images at 1 | Nb images at 2 | <1.4 (%) | ≥1.4 (%) |
| Reader 1 | 59 (10%) | 164 (27%) | 377 (63%) | | |
| Reader 2 | 129 (22%) | 140 (23%) | 331 (55%) | | |
| Reader 3 | 120 (20%) | 194 (32%) | 286 (48%) | | |
| 3 readers | | | | 281 (47%) | 319 (53%) |

TABLE 7

Overall rating of the experts

| | RATING <7 (%) | RATING ≥7 (%) |
|---|---|---|
| Reader 1 | 357 (59.5%) | 243 (40.5%) |
| Reader 2 | 380 (63%) | 220 (37%) |
| Reader 3 | 364 (61%) | 236 (39%) |
| Average of the 3 readers | 379 (63%) | 221 (37%) |

TABLE 8

Inter-observer correlation coefficient for the overall rating

| | Coefficient K |
|---|---|
| Reader 1-Reader 2 | 0.83 |
| Reader 1-Reader 3 | 0.81 |
| Reader 2-Reader 3 | 0.87 |

TABLE 9

Diagnostic performance of the computerized analysis to discriminate between "adequate" and "inadequate" still images

| Numerical parameters | Sensitivity %, [I.C.$_{95\%}$] | Specificity %, [I.C.$_{95\%}$] |
|---|---|---|
| R/G ratio | 84.06 [76.89; 91.23] | 78.67 [70.64; 86.70] |
| Abundance of bubbles | 79.61 [71.71; 87.51] | 73.60 [64.96; 82.24] |
| Brightness | 73.96 [65.36; 82.56] | 78.37 [70.30; 86.44] |
| R/G ratio + abundance of bubbles | 85.24 [78.29; 92.19] | 86.36 [79.63; 93.09] |
| Abundance of bubbles + brightness | 85.20 [78.24; 92.16] | 78.98 [70.99; 86.97] |
| R/G ratio + brightness | 86.12 [76.34; 92.90] | 86.20 [79.44; 92.96] |
| R/G ratio + abundance of bubbles + brightness | 90.01 [84.12; 95.88] | 87.73 [81.30; 94.16] |

REFERENCES

1. McAlindon M E, Ching H-L, Yung D, Sidhu R, Koulaouzidis A. Capsule endoscopy of the small bowel. Ann Transl Med. 2016; 4(19):369.
2. Rokkas T, Papaxoinis K, Triantafyllou K, Pistiolas D, Ladas S D. Does purgative preparation influence the diagnostic yield of small bowel video capsule endoscopy?: A meta-analysis. Am J Gastroenterol. 2009; 104(1):219-27.
3. Ladas S D, Triantafyllou K, Spada C, Riccioni M E, Rey J-F, Niv Y, Delvaux M, de Franchis R, Costamagna G; ESGE Clinical Guidelines Committee. European Society of Gastrointestinal Endoscopy (ESGE): recommendations (2009) on clinical use of video capsule endoscopy to investigate small-bowel, esophageal and colonic diseases. Endoscopy. 2010; 42(3):220-7.
4. Brotz C, Nandi N, Conn M, Daskalakis C, DiMarino M, Infantolino A, Katz L C, Schroeder T, Kastenberg D. A validation study of 3 grading systems to evaluate small-bowel cleansing for wireless capsule endoscopy: a quantitative index, a qualitative evaluation, and an overall adequacy assessment. Gastrointest Endosc. 2009; 69(2): 262-270, 270.e1.
5. Albert J, Göbel C-M, Lesske J, Lotterer E, Nietsch H, Fleig W E. Simethicone for small bowel preparation for capsule endoscopy: a systematic, single-blinded, controlled study. Gastrointest Endosc. 2004; 59(4):487-91.
6. Ninomiya K, Yao K, Matsui T, Sato Y, Kishi M, Karashima Y, Ishihara H, Hirai F. Effectiveness of magnesium citrate as preparation for capsule endoscopy: a randomized, prospective, open-label, inter-group trial. Digestion. 2012; 86(1):27-33.
7. Goyal J, Goel A, McGwin G, Weber F. Analysis of a grading system to assess the quality of small-bowel preparation for capsule endoscopy: in search of the Holy Grail. Endosc Int Open. 2014; 2(3):E183-186.
8. Park S C, Keum B, Hyun J J, Seo Y S, Kim Y S, Jeen Y T, Chun H J, Um S H, Kim C D, Ryu H S. A novel cleansing score system for capsule endoscopy. World J Gastroenterol. 2010; 16(7):875-80.
9. Van Weyenberg S J B, De Leest H T J I, Mulder C J J. Description of a novel grading system to assess the quality of bowel preparation in video capsule endoscopy. Endoscopy. 2011; 43(5):406-11.
10. Abou Ali E, Histace A, Camus M, Gerometta R, Becq A, Nion-Larmurier I, Ulriikka Chaput, Philippe Marteau, Olivier Romain, Christian Florent, Xavier Dray. Development and Validation of a Highly Sensitive and Highly Specific Computed Assessment of Cleansing Score for Small Bowel Capsule Endoscopy. United European Gastroenterology Week. 2016;
11. Moutarde F. Arbres de Décision et Forêts Aléaoires. 2017.
12. Kohavi R. A Study of Cross-validation and Bootstrap for Accuracy Estimation and Model Selection. In: Proceedings of the 14th International Joint Conference on Artificial Intelligence—Volume 2. San Francisco, Calif., USA: Morgan Kaufmann Publishers Inc.; 1995. p. 1137-1143. (IJCAI'95).

The invention claimed is:

1. A device for producing a numerical classifier to determine the visualization quality of endoscopy videocapsule images of a segment of a digestive tract, comprising:
a videocapsule for acquiring a video of segments of the digestive tract;
a memory, coupled to the videocapsule;
a database with videocapsule-extracted images classified during a ground truth step, said extracted images being classified as adequate visualization images and inadequate visualization images, whereby said extracted images are classified according to a score, said score being determined by a visual analysis of the extracted images based on one or more medical criteria, said medical criteria comprising:
(a) a percentage of mucous membrane visualized,
(b) image brightness,
(c) a presence of bubbles,
(d) a presence of bile/chyme, and
(e) a presence of liquids and undigested debris; and
a processor connected to the memory and incorporating the database, said processor being configured to:
calculate at least two numerical parameters, each relating to at least one of said medical criteria used for determining the score, and extracted from the images of the database, the at least two calculated numerical parameters comprising:
a global colorimetric parameter,
a parameter reflecting an abundance of bubbles, and
a parameter reflecting brightness;
perform a statistical machine learning according to a random forest classifier, comprising the steps of:
a) selecting learning images from the extracted images in the database,
b) performing—random drawings of the learning images, wherein each random drawing includes the same number of the learning images,
c) automatically producing a numerical classifier, said numerical classifier being produced with a succession of automatic thresholds applied to the at least two calculated numerical parameters, by numerical analysis of these learning images to construct N binary decision trees, wherein each random drawing produces one binary decision tree,
wherein each binary decision tree is constructed using the at least two calculated numerical parameters, said automatic thresholds being calculated automatically at each node of each binary decision tree based on the at least two calculated numerical parameters that allows for the distribution of said learning images into a first subgroup and into a second subgroup closest to the distribution of the adequate visualization images and the inadequate visualization images, respectively, performed during the ground truth step with the resulting set of binary decision trees constituting said numerical classifier, said numerical classifier being determined to automatically distribute said learning images into the first subgroup of learning images including the largest number of the adequate visualization images and the second subgroup of learning images including the largest number of the inadequate visualization images.

2. The device according to claim 1, wherein the processor is configured to perform a step of numerically deciding the visualization quality of the test images, which is a system for voting on all numerical decisions of the binary decision trees, with each test image having been tested in all the binary decision trees, said test images being the remaining images of the database minus the learning images in the numerical classifiers.

3. The device according to claim 1, wherein the processor is configured to repeat steps b) and c) x times to obtain a final classifier consisting of a plurality of the numerical classifiers resulting from the statistical machine learning and thus having x*N binary decision trees, with N greater than or equal to 100 and x greater than or equal to 10.

4. The device according to claim 1, wherein
the global colorimetric parameter is a red/green ratio of an image when the segment of the digestive tract is a small bowel, or a red/(green+blue) ratio when the segment of the digestive tract is a colon;
the parameter reflecting the abundance of bubbles is:
a textural parameter from a gray-level co-occurrence matrix (GLCM) of a processed image, or
a bubble occupying surface; and
the parameter reflecting brightness is gray-level contrast of an image.

5. The device according to claim 1, wherein the numerical classifier is produced based on the 3 following numerical parameters:
an overall colorimetric parameter, said overall colorimetric parameter being a red/green ratio of an image when the segment of the digestive tract is a small bowel, or a red/(green+blue) ratio when the segment of the digestive tract is a colon;
the parameter reflecting the abundance of bubbles which is:
a textural parameter from a gray-level co-occurrence matrix (GLCM) of a processed image, or
a bubble occupying surface; and
the parameter reflecting the brightness which is a gray-level contrast of an image.

6. A control method applied to a video made by a videocapsule, in at least one segment of the digestive tract of a person, to automatically determine the visualization quality of images of the video, using the numerical classifier of the device according to claim 1, applied to the images of the video, to automatically determine, during an automatic control examination, the images with adequate visualization, the images with inadequate visualization, and a rate of adequate visualization images in the video according to a decision of the numerical classifier.

7. The control method according to claim 6, applied to different persons and further comprising:

a preliminary step of intestinal preparation for the control examination, different for each person;

an automatic examination control step, a step of comparing the efficacy of the different intestinal preparations under examination depending on the rate of the adequate visualization images determined for each different intestinal preparation by the control method.

8. A control device for automatically determining the visualization quality of a video of one or more segments of a person's digestive tract, performed by the device for producing a numerical classifier of claim 1 the control device configured to:

calculate at least two numerical parameters, each relating to one of the following medical criteria, in images of the video, said at least two numerical parameters comprising:

(a) a percentage of mucous membrane visualized, (b) a brightness of the image, (c) a presence of bubbles, (d) a presence of bile/chyme, (e) a presence of liquids and undigested debris; and numerically test the images in the video, and numerically decide the images with adequate visualization, the images with inadequate visualization, and a rate of adequate visualization images in the video according to a decision of the numerical classifier.

* * * * *